(12) United States Patent
Toyota et al.

(10) Patent No.: US 7,344,548 B2
(45) Date of Patent: Mar. 18, 2008

(54) MICRO-PNEUMATIC SNARE

(75) Inventors: Eiji Toyota, Okayama (JP); William M. Chilian, Covington, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 270 days.

(21) Appl. No.: 11/071,617

(22) Filed: Mar. 3, 2005

(65) Prior Publication Data

US 2006/0200193 A1 Sep. 7, 2006

(51) Int. Cl.
*A61M 29/00* (2006.01)
(52) U.S. Cl. .......................... 606/192; 128/898; 600/16
(58) Field of Classification Search ........ 606/190–192, 606/200, 203; 600/101, 104; 604/164.02, 604/164.06, 164.08, 164.1, 164.11, 167.01, 604/167.02
See application file for complete search history.

(56) References Cited

U.S. PATENT DOCUMENTS

| | | | | |
|---|---|---|---|---|
| 3,730,186 A * | 5/1973 | Edmunds et al. | ............ | 606/158 |
| 4,619,261 A | 10/1986 | Guerriero | .................... | 606/194 |
| 4,950,276 A * | 8/1990 | Vince | .................... | 606/158 |
| 6,401,720 B1 | 6/2002 | Stevens et al. | ............. | 128/898 |
| 2002/0147462 A1 | 10/2002 | Mair et al. | .................. | 606/213 |
| 2004/0059403 A1* | 3/2004 | Massullo | .................... | 607/119 |
| 2006/0030920 A1* | 2/2006 | Ben-Muvhar | ............... | 623/1.3 |

OTHER PUBLICATIONS

The Merck Manual of Medical Information, 2nd Home Edition, "Occlusive Peripheral Arterial Disease," pp. 216-224.
Toyota, E. et al., "Vascular endothelial growth factor is required for coronary collateral growth under repetitive myocardial ischemia in the rat," presentation to be made at the Annual Scientific Session of the American College of Cardiology (Orlando, FL, Mar. 6-9, 2005).

* cited by examiner

*Primary Examiner*—Todd E. Manahan
*Assistant Examiner*—Elizabeth Houston
(74) *Attorney, Agent, or Firm*—John H. Runnels; Bonnie J. Davis; James C. Carver

(57) ABSTRACT

A surgical instrument and method are disclosed for enhancing the overall performance of arterial occludes, by allowing the repetitive obstruction of blood flow to a targeted organ or tissue (e.g., heart muscle, brain, kidney, gastrointestinal tissue, leg muscles, arm muscles, other skeletal muscles, or tumors), while reducing the potential for side effects such as gangrene or infarction and for post-implantation movement of the occlude during ischemia. The micro-pneumatic snare allows the repeated occlusion (i.e., the iterated obstruction or closure of a passageway or vessel) of targeted vessels to deprive a selected organ or tissue of blood and oxygen profusion, while the patient may, in general, remain conscious. The micro-pneumatic snare also allows for the stimulation of functional response adjustments in targeted tissues and organs, such as angiogenesis and collateral vessel growth in response to repetitive per fusion obstruction. Alternatively, or in addition, it may be used in the diagnosis of medical conditions associated with inhibited per fusion (e.g., ischemia-repercussion injuries) in heart muscle, or other tissues or organs.

1 Claim, 4 Drawing Sheets

MICRO-PNEUMATIC SNARE

The development of this invention was funded in part by the Government under grant number HL65203 awarded by the National Institutes of Health. The Government has certain rights in this invention.

This invention relates to an apparatus and method for repetitively obstructing the flow of blood and per fusion to a targeted mammalian organ or tissue (e.g., heart muscle, brain, kidney, gastrointestinal organs, skeletal muscle, leg, arm, or tumor).

Peripheral arterial occlusive disease ("PAOD") is a condition involving the gradual synopsis (i.e., constricting or narrowing) or sudden blockage of an artery. Synopsis of an artery is usually caused by atherosclerosis, in which deposits of cholesterol and other fatty materials (e.g., at-home and atherosclerosis plaques) develop in the walls of the artery. This condition is a common disease. For example, it affects approximately 20 percent of people over age 70. PAOD is also common among people who have a family history of atherosclerosis, high blood pressure, high cholesterol levels, or high homo cysteine levels. Ischemia may develop as an artery constricts, if the blood flow does not meet the metabolic demands of the organ or tissue that the artery supplies. Ischemia occurs commonly (but by no means exclusively) in leg muscles. In the last few years, research has been very active in developing techniques for treating ischemia of various organs and tissues (e.g., heart, brain, kidney, muscle), and in determining why ischemic injuries occur. See, in general, "Occlusive Peripheral Arterial Disease," The Merck Manual of Medical Information, $2^{nd}$ Home Edition.

A common therapeutic procedure for treating some types of ischemia, balloon angioplasty, is to insert a catheter with a balloon at its tip into the constricted part of the artery, and then to inflate the balloon to open the blocked region. A permanent sent is then often deployed to help keep the artery open. This procedure is not well-suited for treating multiple occlusions in a peripheral artery if too many areas of the artery are narrowed, which is often the case with leg ischemia. This procedure may also cause vascular intimacy thickening, or restenosis, leading once again to a narrowed artery, sometimes in just a matter of weeks or months.

Another common therapeutic procedure for treating some types of ischemia is bypass surgery, which involves the refuting of blood around the affected artery. A vein or artery taken from another part of the body is grafted to the blocked artery. This procedure is also not well-suited for treating multiple occlusions in a peripheral artery.

Another procedure for treating ischemia involves therapeutic angiogenesis and collateral development, which is usually induced by artery ligation. The principal artery supplying blood to an organ or tissue is surgically ligated with a suture. Arterial ligation may. Indeed induce the formation of new vessels, but it is not yet suited for clinical purposes because it may cause serious side effects, including gangrene or infarction.

Researchers have also evaluated techniques for treating ischemia-repercussion injuries to organs and performing angiogenesis to treat prolonged ischemia using physiological, histologically, and molecular parameters involving the application of biochemical factors such as vasoactive agents, radioactive oxygen species, and cytokines. However, for clinical purposes, these biochemical factors may be rendered ineffective in patients who require invasive surgery and general anesthesia.

U.S. Pat. Pub. No. 2002/0147462 describes methods for preventing or substantially diminishing airflow into a bronchial tube using a variety of devices such as ball bearings, balloons, umbrellas, and preformed bodies shaped to allow them to be wedged or adhered to a lumen of a bronchial tube. In another embodiment, a mixture comprising a thickener or filler mixed with a biocompatible composition is ejected into the lumen of a bronchial tube to prevent airflow to a region of the lung.

U.S. Pat. No. 6,401,720 describes a device and method for facilitating thoracoscopic access into the interior of a beating heart, comprising a tubular access device having an inner lumen for penetration and placement of the device through the muscular wall of the heart, and a means for sealing the penetrated area. The sealing means may comprise a balloon or flange placed on the access device, or a suture placed in the heart wall to gather heart tissue against the access device.

U.S. Pat. No. 4,619,261 describes a hydrostatic pressure device for stopping a bleeding wound, comprising an expansible, flexible container or balloon connected to a tube surrounded by a net or bag made from an open weave fabric which is used to position and secure the balloon over an internal wound so that when the balloon is filled with a fluid, it applies direct pressure to the bleeding wound to stop the blood flow.

An unfilled need exists for a surgical instrument or method for blocking the supply of blood to an organ or tissue, to induce the formation of new vessels, while minimizing the likelihood of side effects such as gangrene or infarction.

We have discovered a surgical instrument and method for enhancing the overall performance of arterial occludes, by allowing the repetitive obstruction of blood flow to a targeted organ or tissue (e.g., heart muscle, brain, kidney, gastrointestinal tissue, leg muscles, arm muscles, other skeletal muscles, or tumors), while reducing the potential for side effects such as gangrene or infarction and for post-implantation movement of the occlude during ischemia. The novel "micro-pneumatic snare" allows for the repeated occlusion (i.e., the iterated obstruction or closure of a passageway or vessel) of targeted vessels to deprive a selected organ or tissue of blood and oxygen per fusion, while the patient may, in general, remain conscious. The micro-pneumatic snare also allows for the stimulation of functional response adjustments in targeted tissues and organs, such as angiogenesis and collateral vessel growth in response to repetitive per fusion obstruction. Alternatively, or in addition, it may be used in the diagnosis of medical conditions associated with inhibited per fusion (e.g., ischemia-repercussion injuries) in heart muscle, or other tissues or organs.

The micro-pneumatic snare comprises a sheath with an expandable device (e.g., a balloon) capable of being adjustable inflated, and an attached constrictor (e.g., a filament). The expandable device may be filled with a fluid (e.g., saline, air, nitrogen, $CO_2$) using a filling tube (e.g., a catheter). The micro-pneumatic snare is implanted adjacent to the targeted vessel. Once the micro-pneumatic snare is positioned near the targeted vessel, the constrictor is looped around both the vessel and the expandable device, for example through slits in the sheath, and the expandable device may be inflated to compress the volume of the targeted vessel and inhibit blood per fusion to the targeted organ, and then deflated to again permit blood flow. In a preferred embodiment, the constrictor is also looped around tissue surrounding the targeted vessel to help reduce post-implantation movement of the sheath during inflation and deflation, so that the targeted vessel may be compressed repeatedly at essentially the same location.

Figure 1:
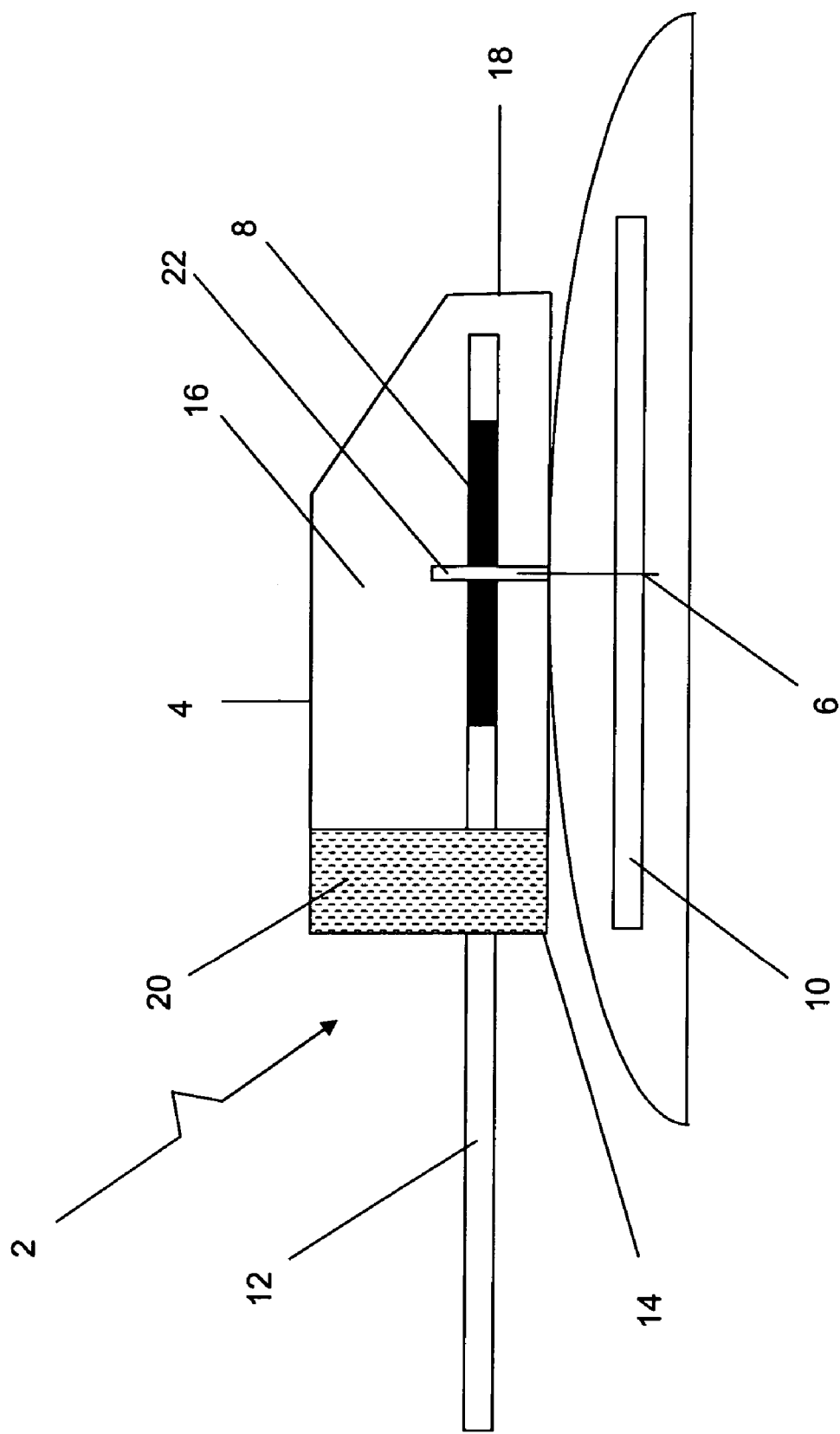
FIG. 1 illustrates a side plan view of one embodiment of the micro-pneumatic snare with a deflated expandable device.

The invention provides a reliable, inexpensive method for repetitively occluding targeted tissues or organs (e.g., heart muscle, brain, kidney, gastrointestinal tissue, arm muscles, leg muscles, other skeletal muscles, or tumors), and performing diagnostic procedures to determine medical conditions associated with the deprivation of per fusion (e.g., ischemia-repercussion injuries). Candidates for this minimally invasive procedure include patients both under and over 70 years old, with diseases related to congestive heart failure, shock from myocardial infarction, or brain ischemia, including patients whose general state of health might not permit general anesthesia or invasive surgery. The apparatus comprises a sheath having an expandable device (e.g., a balloon) capable of being inflated, deflated, and adjusted, and an attached constrictor (e.g., a filament). In operation, once the micro-pneumatic snare is inserted through the skin and muscle in the vicinity of the targeted organ, the constrictor is fastened around both the targeted blood vessel and the sheath. If desired, the expandable device may then be advanced along the vessel to a position closer to the targeted organ or tissue.

In a preferred embodiment, a sheath with two or more slits retains the expandable device in position against the targeted vessel after inflation. The degree of restriction of the targeted vessel is adjusted by inflating or deflating the expandable device. The pressure in the expandable device is adjusted by introducing or releasing a fluid (e.g., saline, air, nitrogen, or $CO_2$) through a filling tube (e.g., a catheter) to compress the targeted vessel. In one embodiment, the filling tube is accessed externally through a tube inlet. This method is referred to as "open-end tubing." Fluid flows through the tube inlet into the expandable device. Fluid may be removed by reversing the process. To avoid infections, the open-end tubing system should only be used for short-term occlusions (less than about one week) with daily sterilizing. In another embodiment, fluid is injected into the filling tube using an automated inflation/deflation pump implanted underneath the skin to reduce occurrence of infections. This system is referred to as "close-end tubing."

To reduce post-implantation movement, the tip of the sheath may be tapered to help anchor the micro-pneumatic snare in a chamber near the targeted organ, to help reduce friction and compressive forces between the sheath and other tissues (e.g., heart muscle) in the vicinity. Doing so helps minimize tissue degeneration and sores from frictional contact and any pressure exerted on surrounding tissues, and helps with repeated ischemia to a target tissue by cycles of inflating and deflating the expandable device, including in a conscious patient. In a preferred embodiment, post-implantation movement may be reduced further by mounting the expandable device on the upper or lower portion of the sheath, placing it on the side nearest the targeted vessel, or stabilizing the apparatus by lowering its center of gravity, depending on the location of the implant site and the patient's posture.

The constrictor is sized and shaped to fit around both the targeted vessel and the sheath, and to compress the vessel as the expandable device is inflated. Optionally, a plurality of apparatuses in accordance with this invention may be used to restrict the blood flowing to a tissue or organ. In this embodiment, the filling tubes may optionally be placed inside a single catheter or other large tubing so that only one tube passes through the body. The several expandable devices may be inflated independently or concurrently.

There are several advantages to the novel apparatus. Degeneration of tissues surrounding a targeted vessel is minimized, because the flow of blood may be re-established periodically. The device securely and stably occludes targeted arteries. The potential need to re-orientate the expandable device following implantation is minimized because its design reduces post-implantation movement. The orientation and shape of the sheath help reduce post-implantation movement, and promote consistent occlusion of the targeted vessel each time the expandable device is inflated. Sealing the front and rear ends of the sheath helps to inhibit fibrous or other tissue from infiltrating the interior surface of the sheath.

EXAMPLE 1

Figure 2:
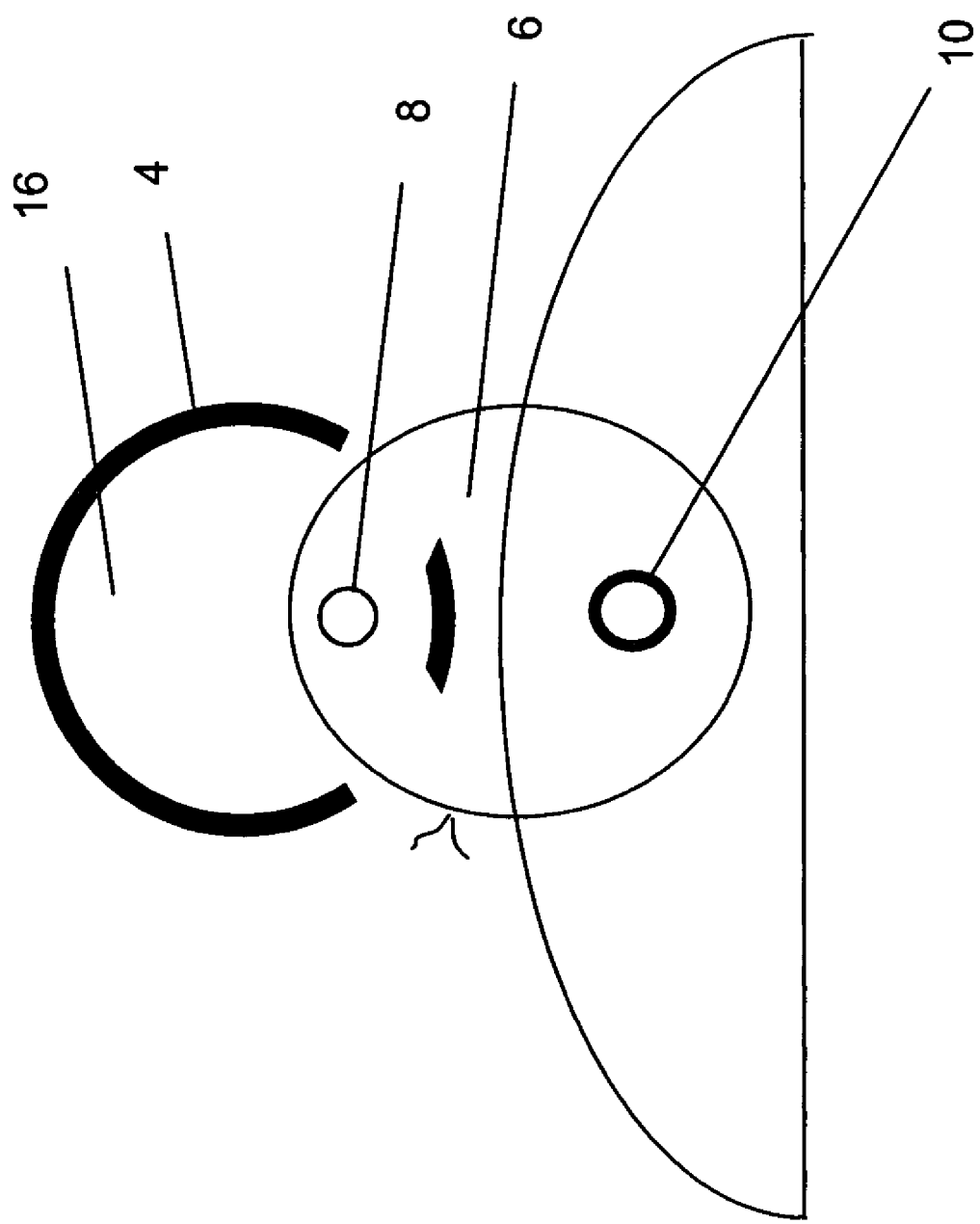
FIG. 2 illustrates a front plan view of one embodiment of the micro-pneumatic snare with a deflated expandable device and a constrictor overlapping a targeted vessel.
Figure 3:
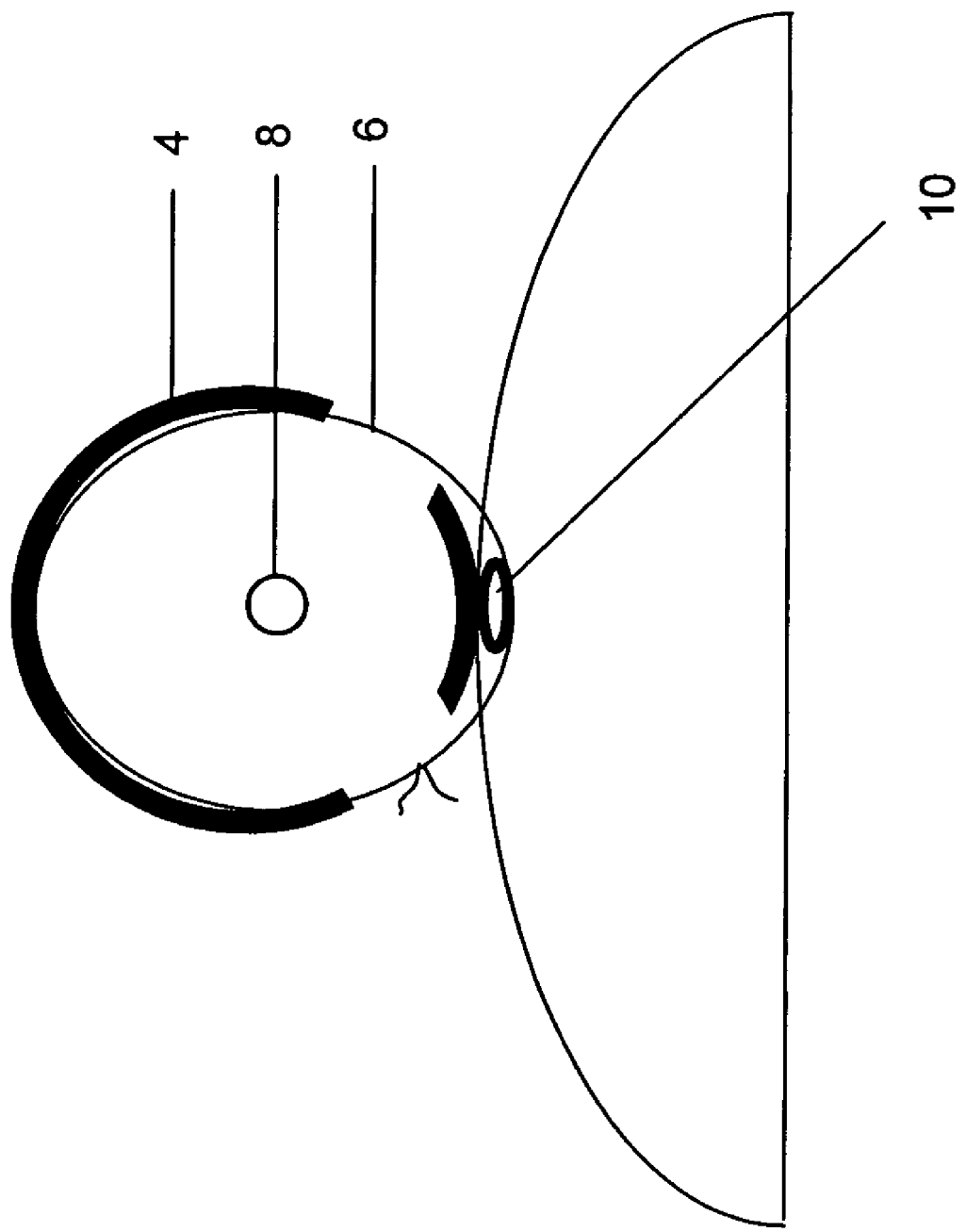
FIG. 3 illustrates a front plan view of one embodiment of the micro-pneumatic snare with an inflated expandable device and a constrictor overlapping a targeted, occluded vessel.

FIG. 1 illustrates a side plan view of one embodiment of novel micro-pneumatic snare 2, in accordance with the present invention. In this embodiment, micro-pneumatic snare 2 comprises a sheath 4, a constrictor 6, and an expandable device 8. Constrictor 6 was sized and shaped to overlap expandable device 8 and to circumscribe a targeted vessel 10 such that when fluid was injected into expandable device 8 through filling tube 12, the targeted vessel 10 was compressed against sheath 4, thus restricting per fusion to the targeted organ or tissue by vessel 10. See e.g., FIGS. 2 and 3. Expandable device 8 and sheath 4 were sized and shaped to complement each other, so that when the expandable device 8 was inflated, post-implantation movement was minimized. In a preferred embodiment, sheath 4 is anchored to tissue surrounding the targeted vessel 10 to further reduce post-implantation movement by circumscribing both the targeted vessel 10 and surrounding tissue with constrictor 6.

As shown in FIG. 1, sheath 4 comprises a base 14, an inner chamber 16, and a tapered tip 18 for placement at a location near the targeted vessel. In this embodiment, sheath 4 was sized and shaped to circumscribe expandable device 8 and to fit within a cavity of the body, in a prototype example, between the chest wall and the base of the heart-base of a small mammal (e.g., a rodent), to anchor sheath 4 to the chest wall and to minimize the pressure exerted on the heart. To inhibit fibrous or other tissues from infiltrating sheath 4, base 14 was sealed with lid 20, which included an access channel (not shown) that complemented the size and shape of filling tube 12; and expandable device 8 was positioned near the bottom center of inner chamber 16 to stabilize the positioning of micro-pneumatic snare 2.

As shown in FIG. 1, sheath 4 further comprised two slits 22 positioned along the circumference of sheath 4, towards the middle. The size and shape of each slit 22 were adapted so that sheath 4 would completely retain expandable device 8, both before and after inflation, and so that constrictor 6

Figure 4:
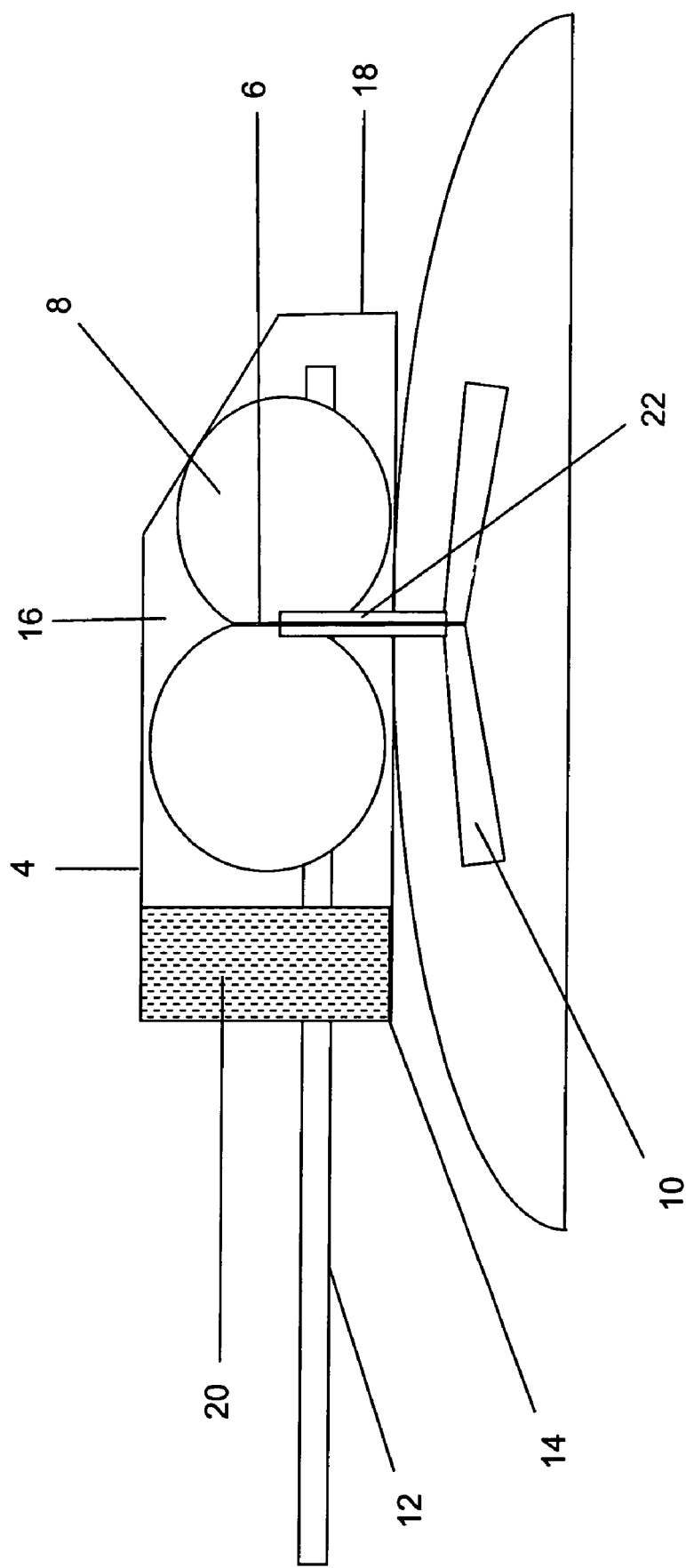
FIG. 4 illustrates a side plan view of one embodiment of the micro-pneumatic snare with an inflated expandable device, occluding the targeted vessel.

(e.g., a filament) could pass from one slit 22 to the other, passing over expandable device 8 and around the bottom, external surface of sheath 4. To facilitate the occlusion of targeted vessel 10, and to minimize post-implantation movement, slits 22 were positioned to maximize compression on the targeted vessel 10 via constrictor 6. In a prototype embodiment, one slit 22 was placed on each side of sheath 4, extending from an imaginary horizontal line passing through the center of sheath 4 to approximately 45° below the horizontal line. See FIG. 4. Sheath 4 is preferably formed from a durable material such as a polyurethane elastomer.

As shown in FIG. 1, filling tube 12 was connected to the interior of expandable device 8 to allow for inflation with fluid. Filling tube 12 was sized and shaped to allow for the injection, retraction, and transport of fluid to expandable device 8. Filling tube 12 should be made of a non-distensible, flexible, biocompatible material, such as a polyurethane elastomer, polyethylene, or other polymer. Optionally, when multiple micro-pneumatic snares are simultaneously used to occlude a targeted tissue or organ, an access device (not shown) with multiple ports, one port attached to the inlet of each filling tube, may be used to individually inflate and deflate each expandable device. The size and shape of the access device is adapted to allow for a tight seal with filling tube and a fluid carrier (e.g., a hypodermic syringe).

EXAMPLE 2

Construction of Prototype

A prototype micro-pneumatic snare 2 comprising a single expandable device (a balloon) within a sheath was used to conduct tests on rats. This device is shown schematically in FIG. 1. The sheath 4 was constructed from a 0.1 mm thick polyurethane elastomer tube having a length of 12 mm and a diameter of 3.2 mm at the open end. Enclosed tip 18 of sheath 4 was cylindrically-shaped and had a diameter of 1.6 mm. The expandable device 8 was a Fogarty-type balloon catheter (model 2-F; Baiter Health care Corp, Deerfield, Ill.).

Lid 20 was fabricated from polyurethane elastomer having a length of about 3 mm and a diameter of 3.2 mm. It had an access channel located about 7 mm to about 10 mm from the bottom, external surface of sheath.

A slit 22 having a width of about 0.3-0.5 mm was cut through each side of the sheath 4 6 mm from the tip of the sheath. Each slit extended from an imaginary horizontal line passing through the center of sheath to approximately 45° below the horizontal line. See FIG. 2.

A nylon suture 6 was passed from one slit to the other using a 5-0 needle (PROLINE®; Johnson & Johnson, Piscataway, N.J.) Passing over the expandable device 8 in the sheath 4 and around the bottom external surface of sheath 4 such that when the snare 2 was positioned near a targeted vessel, the constrictor (suture) 6 could be tied around the vessel, and fluid injected into expandable device 8 via filling tube 12 to compress the vessel against sheath 4 and restrict the flow of blood through the vessel.

EXAMPLE 3

To confirm that the prototype pneumatic snare was highly effective in repetitively occluding a targeted vessel, while reducing the potential for post-implantation movement of the occlude, occlusion tests were performed in rodents using the prototype of Example 2. The pneumatic snare was implanted into a rat near a coronary artery. Once positioned near the vessel, a constrictor (suture) was looped around both the vessel and the expandable device through slits in the sheath, and was then tied off. The expandable device was then advanced to a position near the heart, with the tapered tip lodged between the inner chest wall and the base of the heart base. The balloon was repeated inflated and deflated to obstruct per fusion to the heart by pulling the vessel against the bottom, external surface of the sheath.

We found the pneumatic snare to be effective in obstructing per fusion while the rats were conscious. Post-implantation movement of the pneumatic snare was minimized by mounting the expandable device on the bottom portion of sheath (i.e., the side nearest the targeted vessel) to lower the center of gravity of micro-pneumatic snare. We observed that when the tip of the sheath was cylindrical, degeneration of the heart muscle was seen in several rats. We found that by tapering the tip, fibrous degeneration and compressive effects on the heart were reduced.

Future tests in animals and humans will confirm that the pneumatic snare is effective in treating patients with peripheral arterial obstructive disease.

The complete disclosures of all references cited in this specification are hereby incorporated by reference. Also incorporated by reference is the complete disclosure of the following presentation, which is not prior art to this patent application: E. Toyota et al., "Vascular endothelial growth factor is required for coronary collateral growth under repetitive myocardial ischemia in the rat," presentation to be made at the Annual Scientific Session of the American College of Cardiology (Mar. 6-9, 2005, Orlando, Fla.). In the event of an otherwise irreconcilable conflict, however, the present specification shall control.

We claim:

1. A method for stimulating therapeutic angiogenesis and collateral development in a targeted tissue or organ, comprising:
   providing an expandable device and a constrictor;
   repeatedly increasing and decreasing the pressure in the interior of the expandable device causing the expandable device to repeatedly switch between the inflated and deflated state, causing the constrictor to repeatedly tighten and loosen around one or more vessels that supply blood to the targeted tissue or organ, and
   continuing said tightening and loosening of the vessels for a time and at a rate sufficient to stimulate therapeutic angiogenesis and collateral development in the targeted tissue or organ.

* * * * *